(12) United States Patent
Reaney et al.

(10) Patent No.: US 8,404,884 B2
(45) Date of Patent: Mar. 26, 2013

(54) PROCESS FOR THE EXTRACTION OF MACROMOLECULES FROM A BIOMASS USING THIN STILLAGE

(75) Inventors: Martin J. Reaney, Saskatoon (CA); Kornsulee Ratanapariyanuch, Saskatoon (CA)

(73) Assignee: University of Saskatchewan, Saskatoon, Saskatchewan (CA)

( * ) Notice: Subject to any disclaimer, the term of this patent is extended or adjusted under 35 U.S.C. 154(b) by 0 days.

(21) Appl. No.: 13/073,055

(22) Filed: Mar. 28, 2011

(65) Prior Publication Data

US 2011/0237778 A1    Sep. 29, 2011

Related U.S. Application Data

(60) Provisional application No. 61/318,017, filed on Mar. 26, 2010.

(51) Int. Cl.
*C07F 9/02* (2006.01)
(52) U.S. Cl. ........................................................ 558/146
(58) Field of Classification Search .................. 558/146
See application file for complete search history.

(56) References Cited

U.S. PATENT DOCUMENTS

| | | | |
|---|---|---|---|
| 4,169,090 A | 9/1979 | Murray et al. | |
| 4,208,323 A | 6/1980 | Murray et al. | |
| 4,418,013 A | 11/1983 | Cameron et al. | |
| 4,435,319 A | 3/1984 | Pearce et al. | |
| 4,889,921 A | 12/1989 | Diosady et al. | |
| 5,658,714 A | 8/1997 | Westfall et al. | |
| 5,844,086 A | 12/1998 | Murray | |
| 5,989,600 A | 11/1999 | Nielsen et al. | |
| 6,537,597 B1 | 3/2003 | Nakamori et al. | |
| 6,800,308 B2 | 10/2004 | Maenz et al. | |
| 6,905,713 B2 | 6/2005 | Diosady et al. | |
| 6,992,173 B2 | 1/2006 | Milanova et al. | |
| 7,090,887 B2 | 8/2006 | Newkirk | |
| 2010/0028484 A1* | 2/2010 | Kriesler et al. | 426/7 |
| 2011/0130586 A1* | 6/2011 | Reaney et al. | 558/146 |

FOREIGN PATENT DOCUMENTS

WO    WO2009067809    6/2009

OTHER PUBLICATIONS

Botti et al., The Journal of Biochemical Chemistry, 1995, 270(35), 20530-20535.
Dowd et al., Journal of Agriculture and Food Chemistry, 1994, 42, 283-288.
Ojowi et al., Canadian Journal of Animal Science, 1996, Vo. 76, 547-553.
Kornsulee Ratanapariyanuch's Thesis (submitted to the University of Saskatchewan library on Apr. 13, 2009).
Mustafa et al., Animal Feed Science and Technology, 1999, 80, 247-256.
Oomah, B.D., Der, T.J., and Godfrey, D.V. (2006). Thermal characteristics from flaxseed (*Linum usitatissimun* L.) protein. Food Chemistry, 98, 733-741.
Wheals et al., Trend in Biotechnology, 1999, 17(12), 482-487.
Wilkie et al., Biomass and Bioenergy, 2000, 19, 63-102.
Kornsulee Ratanapariyanuch's Thesis Abstract (submitted to the University of Saskatchewan library on Apr. 13, 2009).

* cited by examiner

*Primary Examiner* — Maryam Monshipouri
(74) *Attorney, Agent, or Firm* — Bereskin & Parr LLP/S.E.N.C.R.L., s.r.l.; Michael Fenwick

(57) ABSTRACT

A process for the extraction of macromolecules from a biomass material comprising:
  a) contacting the biomass material with a solution comprising thin stillage to provide a slurry comprising undissolved solids, dissolved solids and suspended solids; and
  b) separating undissolved solids from the slurry to provide a solid fraction and a liquid fraction; and
wherein the macromolecules are comprised in the dissolved solids.

18 Claims, 1 Drawing Sheet

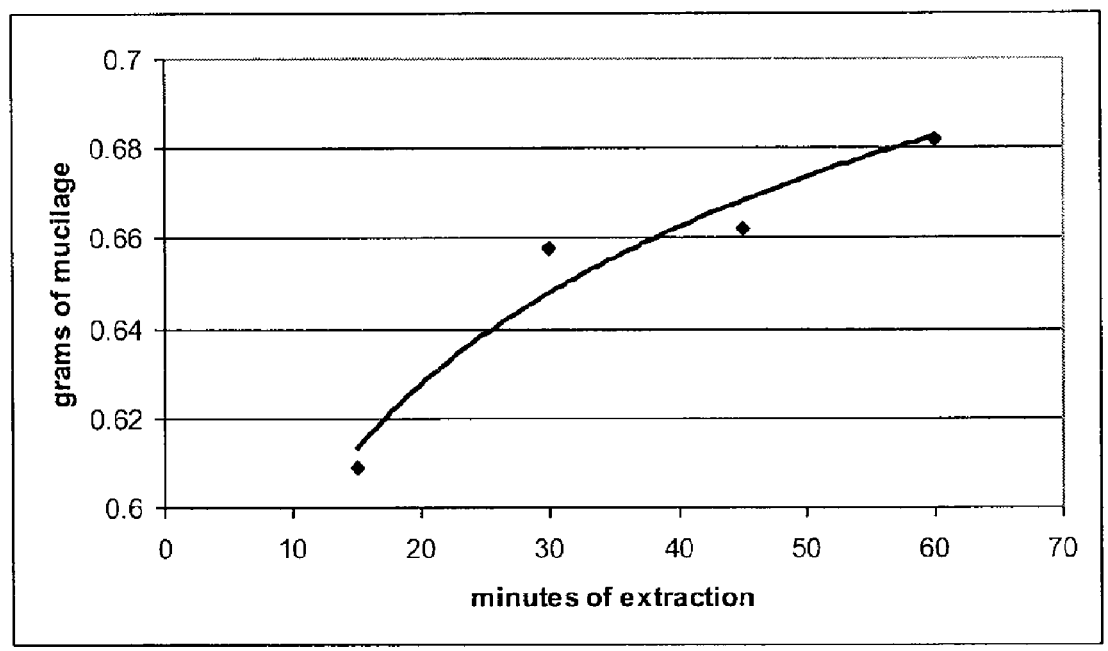

SEQUENCE LISTING

<160> NUMBER OF SEQ ID NOS: 8

<210> SEQ ID NO 1
<211> LENGTH: 10
<212> TYPE: PRT
<213> ORGANISM: Brassica juncea

<400> SEQUENCE: 1

Glu Phe Gln Gln Ala Gln Gln His Leu Arg
1               5                   10

<210> SEQ ID NO 2
<211> LENGTH: 10
<212> TYPE: PRT
<213> ORGANISM: Brassica juncea

<400> SEQUENCE: 2

Ile Tyr Gln Thr Ala Thr His Leu Pro Arg
1               5                   10

<210> SEQ ID NO 3
<211> LENGTH: 12
<212> TYPE: PRT
<213> ORGANISM: Brassica juncea

<400> SEQUENCE: 3

Ile Glu Val Trp Asp His His Ala Pro Gln Leu Arg
1               5                   10

<210> SEQ ID NO 4
<211> LENGTH: 19
<212> TYPE: PRT

```
-continued

<213> ORGANISM: Brassica juncea

<400> SEQUENCE: 4

Gly Leu Pro Leu Glu Val Ile Ser Asn Gly Tyr Gln Ile Ser Pro Gln
1               5                   10                  15

Glu Ala Arg

<210> SEQ ID NO 5
<211> LENGTH: 19
<212> TYPE: PRT
<213> ORGANISM: Brassica juncea

<400> SEQUENCE: 5

Gly Leu Pro Leu Glu Val Ile Ser Asn Gly Tyr Gln Ile Ser Leu Glu
1               5                   10                  15

Glu Ala Arg

<210> SEQ ID NO 6
<211> LENGTH: 8
<212> TYPE: PRT
<213> ORGANISM: Brassica juncea

<400> SEQUENCE: 6

Cys Ser Gly Phe Ala Phe Glu Arg
1               5

<210> SEQ ID NO 7
<211> LENGTH: 13
<212> TYPE: PRT
<213> ORGANISM: Brassica juncea

<400> SEQUENCE: 7

Val Gln Gly Gln Phe Gly Val Ile Arg Pro Pro Leu Arg
1               5                   10

<210> SEQ ID NO 8
<211> LENGTH: 11
<212> TYPE: PRT
<213> ORGANISM: Brassica juncea

<400> SEQUENCE: 8

Gly Pro Phe Gln Val Val Arg Pro Pro Leu Arg
1               5                   10
```

PROCESS FOR THE EXTRACTION OF MACROMOLECULES FROM A BIOMASS USING THIN STILLAGE

This application claims benefit under 35 U.S.C. §119(e) to U.S. provisional application Ser. No. 61/318,017, filed Mar. 26, 2010.

INCORPORATION OF SEQUENCE LISTING

A computer readable form of the Sequence Listing "13764-123_SequenceListing.txt" (1,760 bytes), submitted via EFS-WEB and created on Mar. 28, 2011, is herein incorporated by reference.

FIELD OF THE DISCLOSURE

The present disclosure relates to the extraction of macromolecules from a biomass using solution comprising thin stillage.

BACKGROUND OF THE DISCLOSURE

Yeast fermentation of starch and sugar containing agriculture products such as sugar cane, corn, wheat, barley and sugar beet commonly produces a final solution of ethanol in water and other organic and inorganic compounds called beer. In the fuel ethanol industry and other distilleries, the beer is passed to a distillation column where the ethanol is evaporated leaving a complex aqueous solution of materials that includes ions, organic compounds and other compounds. This material is called stillage. A solid-free clear solution arising from stillage is called thin stillage, which comprises a dilute stream of organic and inorganic compounds. Due to its high biochemical oxygen demand (BOD), it is undesirable to dispose of thin stillage without digestion. In addition, its relatively low value as a nutrient makes it undesirable to concentrate by evaporation.

Thin stillage is usually processed by drying to generate solids called distillers dried grains with solubles (DDGS) that can be used in animal feeds. To make DDGS, thin stillage has to be concentrated into syrup before mixing with wet cake. The process to concentrate thin stillage is not energy efficient as it consumes about 40-45% of the thermal energy required to evaporate and dry thin stillage, and 30-40% of the electrical energy utilized in a dry-grind facility. Accordingly, the energy required to evaporate the large amount of water entrained in thin stillage is a major cost in the ethanol industry. Peyton et al., 2007 (U.S. Pat. No. 7,267,774) teaches an efficient process whereby discharged still bottoms may be filtered in their pasteurized state under sanitary conditions with the water and nutrients directly recovered for beneficial human consumption while the solid concentrate is conveyed to a anaerobic bioreactor that recovers methane to power the pressurized membrane filtration. The need for this process is driven by the significant BOD of the thin stillage making it undesirable to dispose of this stream without digestion and its relatively low value as a nutrient making it undesirable to concentrate by evaporation.

Newkirk et al. (U.S. Pat. No. 7,090,887) disclose a multi-stage extraction protein extraction and recovery process using water and CaO to adjust pH. Diosady et al. (U.S. Pat. No. 4,889,921) extracted 100 g of rapeseed meal with 1,800 g of water. Murray (U.S. Pat. No. 5,844,086) extracted 50 kg of commercial canola meal with 500 L of water. In all of these extractions the percent of protein concentrate recovered to water used in extraction and processing is less than 3%.

Neilsen and Helmer (U.S. Pat. No. 5,989,600) describe using phytase to enhance protein recovery after suspending soy protein concentrate in deionized water at 50° C.

SUMMARY OF THE DISCLOSURE

A process for the extraction of macromolecules from a biomass using thin stillage, which is a by-product of the ethanol industry, has been developed. Accordingly, the present disclosure includes a process for the extraction of macromolecules from a biomass material comprising:
  a) contacting the biomass material with a solution comprising thin stillage to provide a slurry comprising undissolved solids, dissolved solids and suspended solids; and
  b) separating undissolved solids from the slurry to provide a solid fraction and a liquid fraction; and
  c) optionally isolating the dissolved solids from the liquid fraction, optionally isolating the suspended solids from the liquid fraction and/or optionally concentrating the liquid fraction,
wherein the macromolecules are comprised in the dissolved solids.

It is an embodiment of the application that the thin stillage is prepared by:
  a) fermentation of a carbohydrate-rich biomass material using a microorganism in an aqueous solution to provide an ethanol-containing beer;
  b) distilling the beer to remove the ethanol to provide a thin stillage;
  c) optionally removing suspended solids from the thin stillage; and
  d) optionally removing macromolecular solutes from the thin stillage.

In another embodiment, the carbohydrate rich-biomass comprises starch as a major carbohydrate. In a further embodiment, the carbohydrate rich-biomass comprises cellulose as a major carbohydrate. In another embodiment, the carbohydrate rich-biomass comprises sucrose as a major carbohydrate.

In another embodiment, the carbohydrate rich-biomass is a seed. In a further embodiment, the carbohydrate rich-biomass is a cereal. In another embodiment, the cereal is corn, wheat, rice, barley, oats or sorghum or a mixture thereof. In a further embodiment, the carbohydrate rich-biomass is a plant stem or tuber. In a further embodiment, the stem or tuber is from a potato or sweet sorghum.

In another embodiment of the disclosure, the starch in the carbohydrate-rich biomass is converted to glucose by one or more enzymes or catalysts to produce a fermentable sugar.

In an embodiment, the cellulose in the carbohydrate-rich biomass is depolymerized by one or more enzymes or catalysts to produce a fermentable sugar.

In another embodiment of the disclosure, the microorganism used in the fermentation of the carbohydrate-rich biomass is a yeast or a bacterium.

In a further embodiment of the disclosure, the suspended solids are removed from the thin stillage by centrifugation or sedimentation.

In another embodiment, the macromolecular solutes are removed from the thin stillage by ultrafiltration or nanofiltration.

In an embodiment of the disclosure, the pH of the thin stillage is increased above pH 8. In another embodiment, the pH of the thin stillage is adjusted above pH 8 using waste alkaline solution from biodiesel production. In a further embodiment, the waste alkaline solution from biodiesel production is a glycerol/potassium hydroxide solution.

In another embodiment of the disclosure, the pH of the thin stillage is decreased below pH 5.

In a further embodiment of the disclosure, the thin stillage further comprises an additive. In another embodiment, the additive is a salt, detergent or zwitterions or a mixture thereof.

In another embodiment, the slurry of the biomass material and thin stillage is heated to improve extraction of the macromolecules from the biomass.

In another embodiment of the disclosure, the undissolved solids in the slurry of the biomass material and thin stillage are separated by filtration or centrifugation.

In a further embodiment, the dissolved solids in the slurry of the biomass material and thin stillage are isolated by ultrafiltration, diafiltration, reverse osmosis or nanofiltration. In another embodiment, the dissolved solids in slurry of the biomass material and thin stillage are isolated by evaporation. In an embodiment, the dissolved solids are isolated by precipitation.

In a further embodiment of the disclosure, the dissolved solids in slurry of the biomass material and thin stillage are precipitated by a change in pH or ionic strength.

In another embodiment, the contacting of the biomass material with the thin stillage is conducted in a continuous process. In another embodiment, the contacting of the biomass material with the thin stillage is conducted in a batch process.

In another embodiment, the contacting of the biomass material with the thin stillage is conducted in a countercurrent process. In another embodiment, the contacting of the biomass material with the thin stillage is combined with the preparation of the thin stillage in a continuous process.

In another embodiment, the present disclosure also includes a macromolecular concentrate or isolate produced in accordance with the process of the disclosure. In another embodiment, the macromolecules comprise proteins, optionally a protein isolate or a protein concentrate.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The application will now be described in greater detail with reference to the following drawings in which:

FIG. 1 is a graph showing mucilage extraction using $NaHCO_3$ with respect to the time of the extraction.

DETAILED DESCRIPTION (I) Definitions

The term "biomass material" as used herein refers to any biomass in which desirable macromolecules, such as proteins, can be extracted. Examples of biomass include, but are not limited to, an oilseed, plant matter, animal matter, etc. Examples of oilseeds include, but are not limited to, canola seed, rapeseed, mustard seed, flax seed, soybean, nuts such as peanuts, hemp seed, linseed, cotton seed, etc. In an embodiment, the biomass material is a ground, defatted oilseed meal.

The term "thin stillage" as used herein refers to a complex aqueous solution including, but not limited to, ions, organic compounds and other compounds, which is often obtained from the fuel ethanol industry as a common waste byproduct. Thin stillage is produced from the fermentation, by yeast and/or other microorganisms, of starches and sugar, which results in an ethanol containing slurry called a beer. After distillation of the beer to remove the ethanol, a slurry called stillage remains. After filtering the solids from the stillage, a thin stillage is obtained, which is a complex aqueous solution. Compounds that have been identified in a thin stillage include, but are not limited to, carbohydrates, fiber, protein, ash, amino acids, lipids, yeast, yeast metabolites, bacteria, bacterial metabolites, fungi, wheat metabolites and minerals. Yeast metabolites include, but are not limited to, compounds selected from glycerol, ethanol, succinic acid, glycerophosphorylcholine and phenylethyl alcohol. Bacterial metabolites include, but are not limited to, compounds selected from isopropanol, acetic acid, lactic acid and 1,3-propanediol. Wheat metabolites include, but are not limited to, betaines. Minerals include, but are not limited to, calcium chloride, sodium chloride, potassium sulphate, sodium nitrate, magnesium hydroxide, sodium sulphate and potassium hydroxide. In another embodiment, synthetic thin stillages are also produced by combining many, or all, of the above identified compounds.

The term "macromolecule" as used herein refers to any compound present in the biomass which is capable of being extracted with thin stillage. In an embodiment, the macromolecules comprise protein, peptides, gums, mucilaginous compounds, polyphenolic compounds and/or complex polymers of carbohydrates and gums. In another embodiment, the macromolecules comprise protein and/or peptides.

The term "contacting" as used herein refers to the manner in which the solution comprising the thin stillage and the biomass material are intimately combined so that the solution extracts macromolecules, such as proteins, from the biomass. For example, the solution comprising the thin stillage is stirred with the biomass to ensure intimate contact of the solution with the macromolecules in the biomass, and results in a slurry comprising undissolved solids, dissolved solids and suspended solids.

The term "slurry" as used herein refers to a mixture of thin stillage and the biomass material containing macromolecules, that has been sufficiently mixed to form a mixture comprising undissolved solids, dissolved solids and suspended solids.

The term "undissolved solids" as used herein refers to any compounds in the biomass material which are substantially not dissolved by the thin stillage and typically settle to the bottom of the reaction vessel upon standing.

The term "dissolved solids" as used herein refers to any compounds in the biomass material which are substantially dissolved by the thin stillage.

The term "suspended solids" as used herein refers to any compounds in the biomass material which do not dissolve in the thin stillage, but have a molecular weight such that they substantially form a suspension in the thin stillage.

The terms "separating", "removing" and "isolating" as used herein refer to any method of separating and isolating one type of material from another, typically the separation of a solid material from a liquid material or the separation of one or more solid or liquid materials from another. The selection of methods to be used for the separation of solid materials from liquid materials will depend on the size of the solid particles to be separated, as would be known to a person skilled in the art, and include, for example filtration, nanofiltration, osmosis, centrifugation, sedimentation, precipitation, etc. The selection of methods to be used for the separation of one or more liquids or solids from each other will depend on the physical characteristics of the materials, as would be known to a person skilled in the art, and include all forms of chromatography, precipitation, recrystallization, etc.

The term "solid fraction" as used herein refers to the combined undissolved solids that have been separated from the slurry.

The term "liquid fraction" as used herein refers to the solution of thin stillage containing both the dissolved solids and suspended solids.

The phrase "alkaline solution from biodiesel production" as used herein refers to a glycerol by-product of the bio-diesel industry. It will be understood to those skilled in the art that macromolecule extractions, such as protein extractions, using aqueous solutions are improved when the extraction is performed at an alkaline pH. Biodiesel is a fuel produced from triglyceride oils that can be used to fuel diesel engines. Biodiesel is commonly defined as the monoester of a lower aliphatic alcohol and a fatty acid. It is typically produced by trans-esterification (alcoholysis) of triglyceride molecules using a catalyst and a monohydric alcohol (methanol, ethanol, etc.) to form monoesters and glycerol. The trans-esterification reaction utilizes three moles of alcohol to react with one mole of triglyceride. The reaction yields three moles of fatty acid ester and one mole of glycerol. Biodiesel production commonly utilizes either hydroxide or methoxide as the catalyst. Sodium or potassium hydroxide is dissolved in methanol and forms methoxide ions, the actual catalytic agents. Accordingly, a by-product of the bio-diesel industry is alkaline glycerol, which is therefore utilized in an embodiment of the present disclosure to adjust the pH of the protein extraction process. Such alkaline solutions are described in WO2009/067809 to Reaney et al., herein incorporated by reference.

Terms of degree such as "substantially", "about" and "approximately" as used herein mean a reasonable amount of deviation of the modified term such that the end result is not significantly changed. These terms of degree should be construed as including a deviation of at least ±10% of the modified term if this deviation would not negate the meaning of the word it modifies.

(II) Process of the Disclosure

The ethanol fuel industry produces thin stillage as a by-product of the fermentation of starches and carbohydrates. Thin stillage is a complex aqueous solution including, but not limited to, ions, organic compounds and other compounds. The process of concentrating thin stillage by evaporation of the water takes large amounts of energy. During the ethanol production process, the temperature of the thin stillage rises to about 80-85° C. as a result of the ethanol distillation process. Accordingly, in an embodiment, as protein extractions are optionally conducted at increased temperatures, there are large energy savings when thin stillage is used as a macromolecule (such as a protein) extraction medium. In addition, in an embodiment, there are large water savings when thin stillage is used as the extraction medium, for example, in protein extraction, as this industry uses large amounts of water.

Furthermore, in an embodiment, thin stillage contains minerals [Ojowi et al., Canadian Journal of Animal Science, 1996, Vo. 76, 547-553; Mustafa et al., Animal Feed Science and Technology, 1999, 80, 247-256] which may enhance protein extraction, such as the proteins napin and cruciferin. It also contains yeast cells, soluble nutrients and grain protein molecules (Wheals et al., Trend in Biotechnology, 1999, 17(12), 482-487) as protein sources. Therefore, in an embodiment, the protein content of the extracted macromolecules, may increase. Moreover, ethanol residue remains in the thin stillage after the distillation process (Wilkie et al., Biomass and Bioenergy, 2000, 19, 63-102), along with other organic compounds (Dowd et al., Journal of Agriculture and Food Chemistry, 1994, 42, 283-288; Wilkie et al., Biomass and Bioenergy, 2000, 19, 63-102), which might have an inhibitory effect on myrosinase activity (Botti et al., The Journal of Biochemical Chemistry, 1995, 270(35), 20530-20535) in defatted meal, which in an embodiment, would allow more efficient isolation of intact glucosinolates.

In an embodiment, a process for the extraction of macromolecules from a biomass using thin stillage, which is a by-product of the ethanol industry has been developed. Accordingly, the present disclosure includes a process for the extraction of macromolecules from a biomass material comprising:
  a) contacting the biomass material with a solution comprising thin stillage to provide a slurry comprising undissolved solids, dissolved solids and suspended solids; and
  b) separating undissolved solids from the slurry to provide a solid fraction and a liquid fraction; and
  c) optionally isolating the dissolved solids from the liquid fraction, optionally isolating the suspended solids from the liquid fraction and/or optionally concentrating the liquid fraction,
wherein the macromolecules are comprised in the dissolved solids.

It is an embodiment of the application that the thin stillage is prepared by:
  a) fermentation of a carbohydrate-rich biomass material using a microorganism in an aqueous solution to provide an ethanol-containing beer;
  b) distilling the beer to remove the ethanol to provide a thin stillage;
  c) optionally removing suspended solids from the thin stillage; and
  d) optionally removing macromolecular solutes from the thin stillage.

In another embodiment, the carbohydrate rich-biomass comprises starch as a major carbohydrate. In a further embodiment, the carbohydrate rich-biomass comprises cellulose as a major carbohydrate.

In another embodiment, the carbohydrate rich-biomass comprises sucrose as a major carbohydrate.

In another embodiment, the carbohydrate rich-biomass is a seed. In a further embodiment, the carbohydrate rich-biomass is a cereal. In another embodiment, the cereal is corn, wheat, rice, barley, oats or sorghum or a mixture thereof. In a further embodiment, the carbohydrate rich-biomass is a plant stem or tuber. In a further embodiment, the stem or tuber is from a potato or sweet sorghum.

In another embodiment of the disclosure, the starch in the carbohydrate-rich biomass is converted to glucose by one or more enzymes or catalysts to produce a fermentable sugar.

In an embodiment, the cellulose in the carbohydrate-rich biomass is depolymerized by one or more enzymes or catalysts to produce a fermentable sugar.

In another embodiment of the disclosure, the fermentation microorganism is a yeast or a bacterium.

In a further embodiment of the disclosure, the suspended solids are removed from the thin stillage by centrifugation or sedimentation.

In another embodiment, the macromolecular solutes are removed from the thin stillage by ultrafiltration or nanofiltration.

In another embodiment of the disclosure, the pH of the thin stillage is adjusted to increase the efficiency of the extraction of macromolecules from the biomass material. It will be understood by those skilled in the art that by adjusting the pH of the thin stillage, for example to a pH below 5 or a pH above 8, a higher concentration of macromolecules, such as protein, are extracted from the biomass material due to the increased solubility of the macromolecules.

In an embodiment of the disclosure, the pH of the thin stillage is increased above pH 8. In another embodiment, the pH of the thin stillage is adjusted above pH 8 using waste alkaline solution from biodiesel production. In a further embodiment, the waste alkaline solution from biodiesel production is a glycerol/potassium hydroxide solution.

In another embodiment of the disclosure, the pH of the thin stillage is decreased below pH 5.

In a further embodiment of the disclosure, the thin stillage further comprises an additive. In another embodiment, the additive is a salt, detergent or zwitterions or a mixture thereof. It will be understood by those skilled in the art that the addition of additives, such as salt (for example, sodium chloride) increases the efficiency of the extraction of the macromolecules from the biomass material into the thin stillage by increasing the solubility of the macromolecules, such as protein, in the thin stillage.

In another embodiment, the slurry formed by the biomass material and the thin stillage is heated. In another embodiment, the slurry is heated to temperature of between about 10° C. to about 80° C., optionally between about 20° C. to about 60° C., optionally between about 40° C. to about 60° C., optionally between about 40° C. to about 44° C.

In another embodiment of the disclosure, the undissolved solids are separated from the slurry by filtration or centrifugation.

In a further embodiment, the dissolved solids are separated and isolated from the slurry by ultrafiltration, diafiltration, reverse osmosis or nanofiltration. In another embodiment, the dissolved solids are isolated by evaporation. In an embodiment, the dissolved solids are isolated by precipitation.

In a further embodiment of the disclosure, the dissolved solids are precipitated by a change in pH or ionic strength.

In another embodiment, the contacting of the biomass material with the thin stillage is conducted in a continuous process. In another embodiment, the contacting of the biomass material with the thin stillage is conducted in a batch process.

In another embodiment, the contacting of the biomass material with the thin stillage is conducted in a countercurrent process. In another embodiment, the contacting of the biomass material with the thin stillage is combined with the preparation of the thin stillage in a continuous process.

In another embodiment, the present disclosure also includes a macromolecular concentrate produced in accordance with the process of the disclosure. In another embodiment, the macromolecules comprise proteins.

In another embodiment, the biomass material comprises an oilseed. In another embodiment, the oilseed comprises a defatted oilseed meal. In a further embodiment, the defatted oilseed meal comprises defatted canola seed meal, defatted rapeseed meal, defatted mustard seed meal, defatted flax seed meal, defatted soybean meal, defatted peanut meal, defatted hemp seed meal, defatted linseed meal or defatted cotton seed meal.

In another embodiment, the macromolecules comprise protein, peptides, gums, mucilaginous compounds, polyphenolic compounds and complex polymers of carbohydrates and gums. In another embodiment, the macromolecules comprise protein and/or peptides.

In another embodiment of the disclosure, the thin stillage comprises compounds selected from carbohydrates, fiber, protein, amino acids, lipids, yeast, yeast metabolites, bacteria, bacterial metabolites, fungi, wheat metabolites and minerals. In another embodiment, the yeast metabolites comprise compounds selected from glycerol, ethanol, succinic acid, glycerophosphorylcholine and phenylethyl alcohol. In a further embodiment, the bacterial metabolites comprise compounds selected from isopropanol, acetic acid, lactic acid and 1,3-propanediol. In another embodiment, the wheat metabolites comprise betaine.

In another embodiment, before using as the extraction medium for the macromolecules, the thin stillage is filtered to remove other macromolecules which remain after the fermentation process which generates the thin stillage.

Certain embodiments of the invention are disclosed below by way of example.

EXAMPLES

Mustard seed (*Brassica juncea* (L.) Czem) was obtained from Agriculture aand Agri-Food Canada, Saskatoon Research Centre, Saskatoon, SK. All seed was from the 2006 harvest and was grown on plots near Saskatoon. Thin stillage (wheat basis) was provided by Pound-Maker Agventures Ltd., Lanigan, SK. Samples of thin stillage were taken on four collection dates (May 18, May 27, May 28 and Jun. 1, 2007) and were stored at 4° C. (for up to 4 months) until used. However, micro-organisms can possibly grow over the 4 month storage period. Prior to all analysis of physical properties, chemical properties, chemical constituents, micro-organism content and ion content, samples were centrifuged at 1,053×g for 20 minutes at 4° C. (Model Avanti® J-E, Beckman Coulter Canada Inc., Mississauga, ON). Glycerol containing approximately 10 percent KOH was provided from an industrial biodiesel processor (Milligan Biotechnology Inc., Foam Lake, SK).

Example 1

Defatted Meal Preparation

Mustard seed was extracted mechanically using a continuous screw expeller (Komet, Type CA59 C; IBG Monforts Oekotec GmbH & Co., Mönchengladbach, Germany) operated at a speed of 6.5 (approximately 93 rpm) using a 6-mm choke. Oil remaining in the presscake was removed using hexane as a solvent (Milanova et al., 2006; Oomah et al., 2006), and the residual hexane in the defatted meal was removed in a fume hood overnight. Defatted meal was analyzed for protein and oil content.

Protein content was determined on 0.5 g samples using the Kjeldahl method [modified from method 981.10 of the A.O.A.C (1990)]. Samples were digested by heating with concentrated $H_{2SO4}$ in a heating/digestion block using a package of Kjeldahl digestion mixture #200 as a catalyst. After digestion, samples were distilled using a steam distillation unit (Model 320, Büchi Analytical Inc., New Castle, Del.) with 30% (w/v) NaOH. Boric acid (4%) was used to trap ammonia from the distillation. The distillate was titrated with 0.2N HCl using N-Point indicator as an indicator. The nitrogen content was calculated using the equation:

% $N$=(mL of 0.2N HCl sample−mL HCl blank)×normality of HCl×0.014×(1/sample weight×100).

The % N of the sample was converted to % protein content by multiplying % N by 6.25.

Oil content was determined using a Goldfisch Extractor (Model 22166B, LabConCo Corporation, Kansas City, Mo.) [modified from method 960.39(a) of the A.O.A.C (1990)]. Approximately 20 g of sample was ground using a coffee grinder to pass through a 1.0-mm screen (approximately 30 seconds). Three grams of ground sample was weighed on a filter paper (Whatman No. 4) and folded. The samples were placed in cellulose thimbles (25×80 mm, Ahlstrom AT, Holly Spring, Pa.). Samples were extracted for 6 hours using 50 mL of hexane as solvent. The hexane was distilled from the oil extraction beakers, after which the beakers were heated at low temperature (30-40° C.) using a hot plate placed in a fume hood. The beakers were then transferred to an oven (105° C.) for 30 minutes and then allowed to cool to room temperature (approximately 25° C.) in a desiccator.

Moisture content was determined by heating a weighed sample [1 g of ground sample using a coffee grinder to pass through 1.0-mm screen (approximately 30 seconds)] at 100-102° C. for 16-18 hours or until the weight of the sample was constant [modified from method 950.46 B.a, of the A.O.A.C (1990)]. The samples were allowed to cool to room temperature in a desiccator for at least 1 hour before weighing.

Example 2

Extraction of Mustard (*Brassica juncea*) Protein with Water (Comparative Example)

Five grams of ground defatted *B. juncea* meal was mixed with 150 mL of water adjusted salt concentration to 1M. The pH of the mixture was adjusted to pH 10 using KOH dissolved in glycerin (a co-product of biodiesel production). The solution was then stirred for two hours. Subsequently, the solution was centrifuged at 5,000×g for 10 minutes and supernatant was taken for dialysis using Spectra/Por molecular porous membrane tubing at 3,500 molecular weight cut off (MWCO) in the ratio 1:1000 of supernatant to distilled water. Water exchange with fresh deionized water was repeated 3 times a day, until the conductivity of permeate water was equal to that of deionized distilled water after 8 hours of dialysis (approximately 5 days). The solution after dialysis was freeze dried. The extracted protein had protein content (N×6.25) approximately 105% by weight with the protein exaction efficiency being approximately 60%. After that extracted protein was used to examine SDS-PAGE, peptide sequencing, amino acid composition, in vitro digestibility, and lysine availability. The results form SDS-PAGE showed that the molecular weight of extracted protein from water was approximately 14, 18-20, 20-22, 34, and 55 kDa. In addition, the results of peptide sequencing, amino acid composition, and in vitro digestibility and lysine availability are presented in table 1, 2, and 3 respectively.

Example 3

The Extraction of Mustard (*Brassica juncea*) Protein with Thin Stillage

Five grams of ground defatted *B. juncea* meal was mixed with 150 mL of centrifuged filtered thin stillage (centrifuge at 1,053×g for 20 minutes at 4° C., filter through 3,000 molecular weight cut off membrane), which salt level was adjusted to 1M. The pH of the mixture was adjusted to pH 10 using KOH dissolved in glycerin (a co-product of biodiesel production). After that the solution was stirred for two hours. Subsequently, supernatant was taken for dialysis using Spectra/Por molecular porous membrane tubing 3,500 MWCO in the ratio 1:1000 of supernatant to distilled water. Water exchange with fresh deionized water was repeated 3 times a day, until the conductivity of permeate water was equal to that of deionized distilled water after 8 hours of dialysis (approximately 5 days). The protein solution after dialysis was freeze dried. The extracted protein has protein content (N×6.25) approximately 96% by weight with the protein exaction efficiency approximately 56%. Extracted protein was taken for examining gel electrophoresis, amino acid composition, in-vitro digestibility, and lysine availability. The results from SDS-PAGE showed that protein extracted from thin stillage had molecular weight approximately, 14, 18-20, 20-22, 34, and 55 kDa., amino acid content, in-vitro digestibility, and lysine availability of extracted protein are reported in table 4 and 5.

Example 4

The Extraction of Flax Mucilage with Thin Stillage 5 grams of flax seeds were mixed with 40 mL of 0.5M sodium bicarbonate ($NaHCO_3$). The extraction time was varied from 15, 30, 45, and 60 minutes. The mucilage extraction was done at 50° C. and 3 times extraction countercurrently. Each time of extraction the viscous liquid was separated from the flax seeds using syringes and the rest of viscous liquid was separated using a centrifuge at rpm for 40 minutes at 25° C. The liquid from 3 times extraction was collected and the centrifuged thin stillage (3000 rpm for 20 minutes at 4° C.) was added into the viscous liquid at 1:1 ratio. The viscosity of the liquid was measured at 25° C. using a Shell cup No. 1. After that 95% ethanol was added to the liquid at the ratio 1:1. The solution then was stirred for 1 hour for the first washing. The mucilage was separated from the solution using a centrifuge at 6000 rpm for 10 minutes at 4° C. The second wash of mucilage was done using approximately 110 mL of 95% ethanol stirring for 30 minutes. The mucilage was separated from ethanol using a centrifuge at 6000 rpm for 10 minutes at 4° C. The mucilage was then transferred to the moisture tint and was placed in the over at 105° C. overnight was weigh the dry weight. FIG. 1 shows a graph of the grams of mucilage extraction versus the length of the extraction.

5 grams of flax seeds were mixed with centrifuged thin stillage (pH of thin stillage was adjusted to 7 using 30% (w/w) NaOH and centrifuged at 4000 rpm for 40 minutes at 4° C.). 0.5M of $NaHCO_3$ was added into centrifuged thin stillage). The mucilage was extracted for 30 minutes at 50° C. 3 times extraction countercurrently. Each time of extraction the viscous liquid was separated from the flax seed using syringes and the rest of viscous liquid was separated using a centrifuge at rpm for 40 minutes at 25° C. The viscous liquid 3 extractions was collected. The distilled water was added into the viscous liquid at 1:1 ratio. The viscosity of the liquid was measured at 25° C. using a Shell cup No. 1. After that 95% ethanol was added into the liquid at the ratio 1:1 and the solution was stirred for 1 hour. The mucilage was separated from the solution using a centrifuge at 6000 rpm for 10 minutes at 4° C. The second wash of mucilage was done using approximately 110 mL of 95% ethanol stirring for 30 minutes. The mucilage was separated from ethanol using a centrifuge at 6000 rpm for 10 minutes at 4° C. The mucilage was then transferred to the moisture tint and was placed in the over at 105° C. overnight was weigh the dry weight. The results of mucilage extraction using water or thin stillage are present in Table 6.

Example 5

Extraction of Oat Beta Glucan with Thin Stillage

Oat groats (150 g) were abraded until approximately 10% of groat weight had been removed with a laboratory Satake mill, fitted with a #30 stone and a 1.00 mm slotted screen (approximately 20 second). Abraded oat groats (40 g) were steeped in 100 mL of 0.1% sodium metabisulphite at 50° C. for 4 hours during which time the groats rapidly imbibed water to the extent of their own weight. Steeped abraded oat groats were ground with 50% ethanol 3 times (2 minutes/time) using a blender. After each grinding step the mixture was passed through a 250 micron screen to separate the course bran from the finer flour fraction. Subsequently the bran was washed twice with 50% ethanol (at a ratio of 1 part bran to 5 parts solution; 20 minutes/wash) the bran was recovered by screening after each wash. The bran was air dried to yield an oat bran which contains 14-20% of beta glucan.

Oat bran (1.25 g) was slurried in 120 mL of distilled water at 80-90° C. for 1 hour to re-hydrated the gum. The slurry was filtered using grade 50 Veratec Graphic Art cheese cloth. The viscosity of the gum was measured at 25° C. using a Shell cup No. 1. The gum was mixed with 95% ethanol and stirred for 20 minutes. After that the precipitated gum was separated from solution by centrifugation (7,000 rpm for 40 minutes at 4° C.). The precipitated gum was washed 2 more times then was transferred to a foil container for drying. The gum was dried overnight at 105° C.

Oat bran (1.25 g) was slurried in 120 mL of centrifuged thin stillage (pH of the thin stillage was adjusted to 7 using 30% (w/w) NaOH and centrifuged at 4000 rpm for 40 minutes at 4° C.) at 80-90° C. for 1 hour to re-hydrated the gum. The slurry was filtered using cheese cloth. The viscosity of the gum was measured at 25° C. using a Shell cup No. 1. The gum was mixed with 95% ethanol and stirred for 20 minutes. After that the precipitated gum was separated from solution using a centrifuge at 7,000 rpm for 40 minutes at 4° C. The precipitated gum was washed 2 more times then was transferred to foil container for drying. The gum was dried overnight at 105° C. The results of beta glucan extraction using water and thin stillage are shown in Table 7. The viscosity of the gum recovered by thin stillage extraction was approximately the same as the product recovered from water extraction.

Example 6

Extraction and Recovery of Small Particle Starch Using Thin Stillage

Dehulled buckwheat (25 g) was steeped in 50 mL of 1% (w/w) sodium metabisulphite at 45° C. for 72 hours. The steeped buckwheat was then ground three times in a blender using 75 mL of distilled water (2 minutes/time). The slurry was passed through 40, 60, and 400 mesh screens respectively. The starch suspension was then centrifuged at 7,000 rpm for 40 minutes at 4° C. The solution was drained and the starch pellet produced by centrifugation was washed twice with distilled water adjusted pH to 9.5 (using 0.1M NaOH) in a ratio 1 part solid to 3 parts washing solution (20 minutes/wash). After each wash, the starch solution was centrifuged (7,000 rpm; 40 minutes; 4° C.). Washed starch was mixed with distilled water and the pH was adjusted to 9.5 (ratio 1:3) at 40° C. for 2 hours (checked pH every 20 minutes and pH was adjusted using 0.1M NaOH). Starch solution was settled at 4° C. for 90 minutes. After that the supernatant was drained. Starch was washed by mixing with distilled water (ratio 1:3) 20 minutes and settling in the fridge for 90 minutes and the supernatant was drained. Starch was then rewashed 2 more times and was dried out using air dry. The starch was weighted, analyzed for protein content and particle size.

Buckwheat (25 g) was steeped in 50 mL of 1% (w/w) sodium metabisulphite at 45° C. for 72 hours. The steeped buckwheat was ground with thin stillage that had been neutralized to pH 7 then centrifuged (4000 rpm for 40 minutes at 4° C.) to remove suspended solids. The steeped buckwheat was then ground three times in a blender using 75 mL of stillage (2 minutes/time). The starch and bran slurry was passed through 40, 60, and 400 mesh screens in sequence. The starch slurry (material that passed the 400 mesh screen) was then centrifuged at 7,000 rpm for 40 minutes at 4° C. After centrifugation starch pellet was washed with thin stillage adjusted pH to 9.5 at a ratio 1 part starch pellet to three parts thin stillage 2 times (20 minutes/time). After each wash, the starch suspension was centrifuged at 7,000 rpm for 40 minutes at 4° C. Washed starch was mixed with centrifuged thin stillage adjusted pH to 9.5 (ratio 1:3) at 40° C. for 2 hours (checked pH every 20 minutes). Starch solution was settled in a fridge for 90 minutes. After that the supernatant was drained out. Starch was washed by mixing with centrifuged thin stillage adjusted pH to 7 (ratio 1:3) 20 minutes and settling in the fridge for 90 minutes and the supernatant was drained. Starch was then rewashed 2 more times (first time with centrifuged thin stillage and second time with distilled water). The starch was air dried and then weighed. The protein content of the starch was estimated from the nitrogen content and particle size was determined by light scattering. The results of starch extraction using water or thin stillage are presented in Table 8.

TABLE 1

Peptide Sequencing of Protein Extracted with Water

| Subunit mass (kDa) | Fragment sequence | Calculated mass (Da) | Actual mass (Da) | Sequence assignment | position |
|---|---|---|---|---|---|
| 14 | EFQQAQQHLR (SEQ ID NO: 1) | 1155.5785 | 1156.6826 | Allergen B.juncea 1-E | 12-20 |
|  | IYQTATHLPR (SEQ ID NO: 2) | 1198.6458 | 1199.7471 | Allergen B.juncea 1-E | 100-109 |

TABLE 1-continued

Peptide Sequencing of Protein Extracted with Water

| Subunit mass (kDa) | Fragment sequence | Calculated mass (Da) | Actual mass (Da) | Sequence assignment | position |
|---|---|---|---|---|---|
| | IEVWDHHAPQLR (SEQ ID NO: 3) | 1499.7633 | 1500.8756 | Cruciferin | 50-61 |
| | GLPLEVISNGYQISPQEAR (SEQ ID NO: 4) | 2070.0745 | 2071.2039 | Cruciferin | 420-438 |
| 18-20 | GLPLEVISNGYQISPQEAR (SEQ ID NO: 4) | 2070.0745 | 2071.2136 | Cruciferin | 338-386 |
| 20-22 | GLPLEVISNGYQISLEEAR (SEQ ID NO: 5) | 2087.0898 | 2088.1885 | Cruciferin | 66-84 |
| | GLPLEVISNGYQISPQEAR (SEQ ID NO: 4) | 2070.0745 | 2071.1917 | Cruciferin | 368-386 |
| 34 | CSGFAFER (SEQ ID NO: 6) | 972.4124 | 973.4891 | Cruciferin | 62-69 |
| | VQGQFGVIRPPLR (SEQ ID NO: 7) | 1465.8518 | 1466.9407 | Cruciferin | 251-263 |
| | IEVWDHHAPQLR (SEQ ID NO: 3) | 1499.7633 | 1500.8281 | Cruciferin | 50-61 |
| 55 | GPFQVVRPPLR (SEQ ID NO: 8) | 1264.7404 | 1265.7958 | Cruciferin | 288-298 |
| | VQGQFGVIRPPLR (SEQ ID NO: 7) | 1465.8518 | 1466.9131 | Cruciferin | 251-263 |
| | IEVWDHHAPQLR (SEQ ID NO: 3) | 1499.7633 | 1500.8154 | Cruciferin | 50-61 |
| | GLPLEVISNGYQISPQEAR (SEQ ID NO: 4) | 2070.0745 | 2071.1272 | Cruciferin | 420-438 |

TABLE 2

Amino Acids of Protein Extracted with Water

| Amino acid | Protein extracted from water |
|---|---|
| Cysteine | 5.19 ± 0.2 |
| Asparagine | 5.99 ± 0.1 |
| Methionine | 2.26 ± 0.03 |
| Threonine | 3.45 ± 0.2 |
| Serine | 4.24 ± 0.04 |
| Glutamic acid | 23.04 ± 0.7 |
| Glycine | 4.94 ± 0.09 |
| Alanine | 4.32 ± 0.08 |
| Valine | 3.41 ± 2 |
| Isoleucine | 3.81 ± 0.06 |
| Leucine | 7.45 ± 0.07 |
| Phenylalanine | 4.07 ± 0.7 |
| Histidine | 4.54 ± 0.08 |
| Lysine | 5.90 ± 0.3 |
| Arginine | 7.56 ± 0.1 |
| Tryptophan | N |
| Tyrosine | N |
| Aspartic acid | N |
| Proline | N |

TABLE 3

In vitro Digestibility and Lysine Availability of Protein Extracted with Water

| | In vitro digestibility | Lysine availability |
|---|---|---|
| Extracted protein from water | 74.53 ± 0.5 | 41.84 ± 4 |

TABLE 4

Amino Acids of Protein Extracted with Thin Stillage

| Amino acid | Protein extracted from thin stillage |
|---|---|
| Cysteine | 5.27 ± 0.01 |
| Asparagine | 5.41 ± 0.2 |
| Methionine | 2.18 ± 0.2 |
| Threonine | 3.13 ± 0.05 |
| Serine | 3.91 ± 0.1 |
| Glutamic acid | 22.23 ± 0.1 |
| Glycine | 4.59 ± 0.07 |
| Alanine | 3.94 ± 0.08 |
| Valine | 5.97 ± 0.2 |
| Isoleucine | 3.43 ± 0.01 |
| Leucine | 6.62 ± 0.05 |
| Phenylalanine | 3.64 ± 0.08 |
| Histidine | 4.52 ± 0.05 |
| Lysine | 5.18 ± 0.02 |
| Arginine | 7.02 ± 0.05 |

TABLE 4-continued

Amino Acids of Protein Extracted with Thin Stillage

| Amino acid | Protein extracted from thin stillage |
|---|---|
| Tryptophan | N |
| Tyrosine | N |
| Aspartic acid | N |
| Proline | N |

TABLE 5

In vitro Digestibility and Lysine Availability of Protein Extracted with Thin Stillage

| | In vitro digestibility | Lysine availability |
|---|---|---|
| Extracted protein from water | 74.89 ± 0.8 | 43.01 ± 0.3 |

TABLE 6

Mucilage Extraction Using Water or Thin Stillage

| Solvent | Time (minute) | Grams of mucilage (dry weight) | Viscosity of the mucilage (centipoise) |
|---|---|---|---|
| 0.5M NaHCO$_3$ | 15 | 0.61 ± 0.03 | 3.15 ± 0.07 |
| | 30 | 0.66 ± 0.01 | 3.20 ± 0.00 |
| | 45 | 0.67 ± 0.01 | 3.30 ± 0.00 |
| | 60 | 0.68 ± 0.01 | 3.35 ± 0.07 |
| Thin stillage | 30 | 0.58 ± 0.01 | 3.25 ± 0.07 |

TABLE 7

Oat Groat Extraction Using Water or Thin Stillage

| Solvent | Grams of gum (dry weight) | Viscosity of the gum (centipoise) |
|---|---|---|
| Water | 0.31 ± 0.00 | 8.85 ± 0.49 |
| Thin stillage | 0.54 ± 0.01 | 8.50 ± 0.00 |

TABLE 8

Extraction of Buckwheat Using Water or Thin Stillage

| Solvent | Starch content (% w/w) | Protein content (% w/w) | Particle size (μm) |
|---|---|---|---|
| Water | 58.82 ± 4.53 | 1.17 ± 0.08 | 15.53 ± 1.48 |
| Thin stillage | 51.11 ± 1.90 | 2.31 ± 0.10 | 19.97 ± 3.36 |

---

The invention claimed is:

1. A process for the extraction of macromolecules from a biomass material comprising:
   a) contacting the biomass material with a solution comprising thin stillage to provide a slurry comprising undissolved solids, dissolved solids and suspended solids; and
   b) separating undissolved solids from the slurry to provide a solid fraction and a liquid fraction; and
   c) optionally isolating the dissolved solids from the liquid fraction, optionally isolating the suspended solids from the liquid fraction and/or optionally concentrating the liquid fraction,
wherein the macromolecules are comprised in the dissolved solids.

2. The process of claim 1, wherein the thin stillage is prepared by:
   a) fermentation of a carbohydrate-rich biomass material using a microorganism in an aqueous solution to provide an ethanol-containing beer;
   b) distilling the beer to remove the ethanol to provide a thin stillage;
   c) optionally removing suspended solids from the thin stillage; and
   d) optionally removing macromolecular solutes from the thin stillage.

3. The process of claim 2, wherein the carbohydrate rich-biomass comprises starch as a major carbohydrate.

4. The process of claim 2, wherein the carbohydrate rich-biomass comprises cellulose as a major carbohydrate.

5. The process of claim 2, wherein the carbohydrate rich-biomass comprises sucrose as a major carbohydrate.

6. The process of claim 3, wherein the carbohydrate rich-biomass is a seed.

7. The process of claim 6, wherein the carbohydrate rich-biomass is a cereal.

8. The process of claim 3, wherein the carbohydrate rich-biomass is a plant stem or tuber.

9. The process of claim 3, wherein the starch is converted to glucose by one or more enzymes or catalysts to produce a fermentable sugar.

10. The process of claim 4, wherein the cellulose is depolymerized by one or more enzymes or catalysts to produce a fermentable sugar.

11. The process of claim 2, wherein the microorganism is a yeast or a bacterium.

12. The process of claim 2, wherein the macromolecular solutes are removed from the thin stillage by ultrafiltration or nanofiltration.

13. The process of claim 1, wherein the pH of the thin stillage is increased above pH 8.

14. The process according of claim 13, wherein the pH of the thin stillage is adjusted above pH8 using waste alkaline solution from biodiesel production.

15. The process of claim 14, wherein the waste alkaline solution from biodiesel production is a glycerol/potassium hydroxide solution.

16. The process of claim 1, wherein the pH of the thin stillage is decreased below pH 5.

17. The process of claim 1, wherein the dissolved solids are precipitated by a change in pH or ionic strength.

18. The process of claim 2, wherein the contacting of the biomass material with the thin stillage is combined with the preparation of the thin stillage in a continuous process.

* * * * *